United States Patent [19]
Barberich et al.

[11] Patent Number: 6,083,993
[45] Date of Patent: *Jul. 4, 2000

[54] METHOD FOR TREATING BRONCHOSPASM USING OPTICALLY PURE R(−) ALBUTEROL

[75] Inventors: Timothy J. Barberich, Concord; James W. Young, Still River, both of Mass.

[73] Assignee: Sepracor Inc., Marlborough, Mass.

[*] Notice: This patent is subject to a terminal disclaimer.

[21] Appl. No.: 09/466,107

[22] Filed: Dec. 17, 1999

Related U.S. Application Data

[63] Continuation of application No. 09/200,541, Nov. 25, 1998, which is a continuation of application No. 09/063,551, Apr. 21, 1998, Pat. No. 5,844,002, which is a continuation of application No. 08/691,604, Aug. 15, 1996, Pat. No. 5,760,090, which is a continuation of application No. 08/335,480, Nov. 7, 1994, Pat. No. 5,547,994, which is a continuation of application No. 08/163,581, Dec. 7, 1993, Pat. No. 5,362,755, which is a continuation of application No. 07/896,725, Jun. 9, 1992, abandoned, which is a continuation of application No. 07/461,262, Jan. 5, 1990, abandoned.

[51] Int. Cl.$^7$ .................................................. A61K 31/135
[52] U.S. Cl. ............................................................ 514/649
[58] Field of Search .............................................. 514/649

[56] References Cited

FOREIGN PATENT DOCUMENTS

| | | |
|---|---|---|
| 2128258 | of 1983 | Germany . |
| 1298494 | of 1971 | United Kingdom . |
| 2 255 503 | of 1992 | United Kingdom . |

OTHER PUBLICATIONS

Tan et al. "Stereoselective Disposition of Salbutamol Enantiomers . . . " *Clin. Chem. 33*, 1026 (1987).

Brittain et al. "Some observations on the β–adrenoceptor agonist . . . " *Br. J. Pharmac. 48*, 144–147 (1973).

Hartley et al. "Absolute Configuration of the Optical Isomers of Salbutamol" *J. Med. Chem. 12*, 995 (1971).

Hawkins et al. "Relative Potency of (−)– and (±) –Salbutamol on Guinea Pig . . . " *J. Med. Chem. 16*, 856–857 (1973).

Buckner et al. "Studies on the Effects of Enantiomers of Soterenol, Trimetoquinol . . . " *J. Pharm. Exp. Ther. 189*, 616–625 (1974).

Passowicz–Muszynska E. "Effect on beta adrenergic receptors of tachyphylaxis . . . " *Index Medicus* 91:164287.

Pauwels "Effect of corticosteroids on the action of sympathomimetics" *Index Medicus* 86:051970.

Chapman et al. "An anomalous effect of salbutamol in sensitised guinea pigs" *Brit. J. Pharmacol 99*, 66P (1990).

Morley et al. "Effects of (+) and racemic salbutamol on airway responses in the guinea pig" *Brit. J. Pharmacol. 104*, 295P (1991).

Chapman et al. "Racemic mixtures at root of worsening symptoms? Active enantiomers . . . " *TIPS 13*, 231–232 (1992).

Muittari et al. "Comparison of acute bronchodilator effects of oral salbutamol, . . . " *Chem. Abstr. 89*: 123259m (1978).

*Primary Examiner*—Raymond Henley, III
*Attorney, Agent, or Firm*—Heslin & Rothenberg, P.C.

[57] ABSTRACT

The optically pure R(−) isomer of albuterol, which is substantially free of the S(+) isomer, is a potent bronchodilator for relieving the symptoms associated with asthma in individuals. A method is disclosed utilizing the optically pure R(−) isomer of albuterol for treating asthma while minimizing the side effects associated with albuterol.

17 Claims, No Drawings

METHOD FOR TREATING BRONCHOSPASM USING OPTICALLY PURE R(−) ALBUTEROL

CROSS REFERENCE TO RELATED APPLICATIONS

This application is a continuation of our prior copending application Ser. No. 09/200,541, filed Nov. 25, 1998, which is a continuation of application Ser. No. 09/063,551, filed Apr. 21, 1998, now U.S. Pat. No. 5,844,002, which was a continuation of application Ser. No. 08/691,604, filed Aug. 15, 1996, now U.S. Pat. No. 5,760,090, which was a continuation of application Ser. No. 08/335,480, filed Nov. 7, 1994, now U.S. Pat. No. 5,547,994, which was a continuation of application Ser. No. 08/163,581, filed Dec. 7, 1993, now U.S. Pat. No. 5,362,755, which was a continuation of application Ser. No. 07/896,725, filed Jun. 9, 1992 now abandoned, which was a continuation of application Ser. No. 07/461,262, filed Jan. 5, 1990, now abandoned.

BACKGROUND

Albuterol is a drug belonging to the general class of beta-adrenergic compounds. The prime action of beta-adrenergic drugs is to stimulate adenyl cyclase, the enzyme which catalyzes the formation of cyclic-3',5'-adenosine monophosphate (AMP) from adenosine triphosphate (ATP). The cyclic AMP formed mediates the cellular responses. Albuterol acts selectively on beta$_2$-adrenergic receptors to relax smooth muscle tissue, for example, in the bronchial system. Albuterol is most commonly used to treat bronchial spasms associated with asthma and is the active component in well-known commercial bronchodilators such as Proventil and Ventolin.

The form in which albuterol is presently used is a racemic mixture. That is, it is a mixture of optical isomers, called enantiomers. Enantiomers are structurally identical compounds which differ only in that one isomer is a mirror image of the other and the mirror images cannot be superimposed. This phenomenon is known as chirality. Most biological molecules exist as enantiomers and exhibit chirality. Although structurally identical, enantiomers can have profoundly different effects in biological systems: one enantiomer may have a specific biological activity while the other enantiomer has no biological activity at all, or may nave an entirely different form of biological activity.

SUMMARY OF THE INVENTION

The present invention relates to a method of treating bronchial disorders, such as asthma, in an individual, by administering to the individual an amount of optically pure R(−) albuterol which is active in bronchial tissue sufficient to reduce bronchial spasms associated with asthma while minimizing side effects associated with albuterol. The method is particularly useful in treating asthma while reducing side effects, such as central nervous system stimulatory effects and cardiac arrythmia. In these applications, it is important to have a composition which is a potent bronchodilator and which does not exhibit the adverse side effects of many beta-adrenergic drugs. A composition containing the pure R(−) isomer of albuterol is particularly useful for this application because this isomer exhibits these desired characteristics. The present method provides a safe, effective method for treating asthma while reducing undesirable side effects, for example, tremor, nervousness, shakiness, dizziness and increased appetite, and particularly, cardiac arrythmia, typically associated with beta-adrenergic drugs. In children, side effects such as excitement, nervousness and hyperkinesia are reduced when the pure isomer is administered. In addition to the above, at certain levels racemic albuterol can cause teratogenic effects, which are believed to be associated with the S(+) isomer. Administering the pure isomer reduces the teratogenic potential which is associated with the S(+) isomer of albuterol.

DETAILED DESCRIPTION OF THE INVENTION

The present invention relies on the bronchodilation activity of the R(−) enantiomer of albuterol to provide relief from bronchial disorders, while simultaneously reducing undesirable side effects, for example, central nervous system stimulatory effects and cardiac disorders, commonly experienced by albuterol users. In the present method, the optically pure R(−) isomer of albuterol, which is substantially free of the S(+) enantiomer, is administered alone, or in combination with one or more other drug(s) in adjunctive treatment, to an individual in whom asthma relief (e.g., relief from bronchial spasms, shortness of breath) is desired. The optically pure R(−) isomer of albuterol as used herein refers to the levorotatory optically pure isomer of $\alpha^1$[(tert-butylamino) methyl]-4-hydroxy-mxylene-$\alpha$, $\alpha$'-diol, and to any biologically acceptable salt or ester thereof. The terms "optically pure" or "substantially free of the S(+) enantiomer" as used herein means that the composition contains at least 90% by weight of the R(−) isomer of albuterol and 10% by weight or less of the S(+) isomer. Optically pure albuterol is readily obtainable by methods known to those of skill in the art, for example, by synthesis from an optically pure intermediate.

In the present method, the R(−) isomer of albuterol is administered to an individual who has asthma. For example, R(−) albuterol is administered to an individual after onset of asthma to reduce breathing difficulty resulting from asthma. In another embodiment, optically pure R(−) albuterol is administered prophylactically, that is, before the bronchiospasm begins in an asthma attack, to prevent its occurrence or to reduce the extent to which it occurs.

In the present method, R(−) albuterol can be administered by inhalation, by subcutaneous or other injection, orally, intravenously, topically, parenterally, transdermally, rectally or via an implanted reservoir containing the drug. The form in which the drug will be administered (e.g., inhalant, powder, tablet, capsule, solution, emulsion) will depend on the route by which it is administered. The quantity of the drug to be administered will be determined on an individual basis, and will be based at least in part on consideration of the individual's size, the severity of the symptoms to be treated and the result sought. In general, quantities of optically pure R(−) albuterol sufficient to reduce the symptoms of asthma will be administered. The actual dosage (quantity administered at a time) and the number of administrations per day will depend on the mode of administration, for example, by inhaler, nebulizer or oral administration. About 30 mcg to about 90 mcg of the optically pure R(−) isomer of albuterol given by inhalation one or more times per day will be adequate in most individuals to produce the desired bronchodilation effect. For oral administration, e.g., tablet or syrup, a dose of about 1 mg to about 8 mg two to four times daily is administered to produce the desired effect.

In the method of the present invention, the optically pure R(−) isomer of albuterol can be administered together with one or more other drug(s). For example, an antiasthmatic drug such as theophylline or terbutaline, or an antihistamine or analgesic such as aspirin, acetaminophen or ibuprofen, can be given with or in close temporal proximity to administration of optically pure, R(−) albuterol. The two (or more) drugs (the optically pure active isomer of albuterol and another drug) can be administered in one composition or as two separate entities. For example, they can be administered in a single capsule, tablet, powder, or liquid, etc. or as individual compounds. The components included in a particular composition, in addition to optically pure albuterol and another drug or drugs, are determined primarily by the manner in which the composition is to be administered. For example, a composition to be administered in inhalent form can include, in addition to the drug(s), a liquid carrier and/or propellant. A composition to be administered in tablet form can include a filler (e.g., lactose), a binder (e.g., carboxymethyl cellulose, gum arabic, gelatin), an adjuvant, a flavoring agent, a coloring agent and a coating material (e.g., wax or a plasticizer). A composition to be administered in liquid form can include the combination of drugs and, optionally, an emulsifying agent, a flavoring agent and/or a coloring agent.

In general, according to the method of the present invention, the optically pure R(−) isomer of albuterol, alone or in combination with another drug(s), is administered to an individual periodically as necessary to reduce symptoms of asthma.

The present composition and method provide an effective treatment for asthma while minimizing the undesirable side effects associated with albuterol use. These side effects include central nervous system effects, such as tremor, nervousness, shakiness, dizziness and increased appetite, and cardiac effects, such as cardiac arrythmia. In children, side effects, such as excitement, nervousness and hyperkinesia, are reduced when the pure isomer is administered. In addition, teratogenic effects associated with albuterol are believed to reside in the S(+) enantiomer. Thus, administering the pure R(−) isomer may reduce the teratogenic potential associated with albuterol.

EQUIVALENTS

Those skilled in the art will recognize, or be able to ascertain, using no more than routine experimentation, many equivalents to the specific embodiments of the invention described herein. Such equivalents are intended to be encompassed in the scope of the following claims.

What is claimed is:

1. A method of treating bronchospasm in a patient with reversible obstructive airway disease, comprising administering to said patient a therapeutically effective amount of optically pure R-(−) albuterol.

2. A method according to claim 1, wherein the albuterol comprises at least 90% by weight of the R(−) isomer and not more than 10% by weight of the S(+) isomer.

3. A method according to claim 1, wherein the albuterol comprises at least 99% by weight of the R(−) isomer and 1% or less by weight of the S(+) isomer.

4. A method according to claim 1, wherein the optically pure R(−) albuterol is administered by inhalation.

5. A method according to claim 4, wherein the optically pure R(−) albuterol is administered in an amount of about 30 $\mu$g to about 90 $\mu$g.

6. A method according to claim 1, wherein the optically pure R(−) albuterol is administered orally.

7. A method according to claim 6, wherein the optically pure R(−) albuterol is administered in an amount of about 1 mg to about 8 mg.

8. A method according to claim 6, wherein the optically pure R(−) albuterol is administered as a tablet, capsule or syrup.

9. A method according to claim 7, wherein the optically pure R(−) albuterol is administered as a syrup.

10. A method of preventing bronchospasm in a patient with reversible obstructive airway disease, comprising administering to said patient a therapeutically effective amount of optically pure R-(−) albuterol.

11. A method according to claim 10, wherein the albuterol comprises at least 90% by weight of the R(−) isomer and not more than 10% by weight of the S(+) isomer.

12. A method according to claim 10, wherein the albuterol comprises at least 99% by weight of the R(−) isomer and 1% or less by weight of the S(+) isomer.

13. A method according to claim 10, wherein the optically pure R(−) albuterol is administered by inhalation.

14. A method according to claim 13, wherein the optically pure R(−) albuterol is administered in an amount of about 30 $\mu$g to about 90 $\mu$g.

15. A method according to claim 10, wherein the optically pure R(−) albuterol is administered orally.

16. A method according to claim 15, wherein the optically pure R(−) albuterol is administered in an amount of about 1 mg to about 8 mg.

17. A method according to claim 15, wherein the optically pure R(−) albuterol is administered as a tablet, capsule or syrup.

* * * * *